(12) United States Patent
Quintaine

(10) Patent No.: US 11,267,776 B2
(45) Date of Patent: Mar. 8, 2022

(54) CYCLOPROPYL RING OPENING BY ALPHA ALKYLATION OF AN ALDEHYDE WITH A POLYCYCLIC OLEFIN

(71) Applicant: FIRMENICH SA, Satigny (CH)

(72) Inventor: Julie Quintaine, Satigny (CH)

(73) Assignee: FIRMENICH SA, Geneva (CH)

( * ) Notice: Subject to any disclaimer, the term of this patent is extended or adjusted under 35 U.S.C. 154(b) by 0 days.

(21) Appl. No.: 16/972,081

(22) PCT Filed: Oct. 14, 2019

(86) PCT No.: PCT/EP2019/077791
§ 371 (c)(1),
(2) Date: Dec. 4, 2020

(87) PCT Pub. No.: WO2020/078909
PCT Pub. Date: Apr. 23, 2020

(65) Prior Publication Data
US 2021/0230089 A1    Jul. 29, 2021

(30) Foreign Application Priority Data

Oct. 16, 2018  (EP) .................................. 18200658

(51) Int. Cl.
*C07C 45/68* (2006.01)
*C11B 9/00* (2006.01)
*C07C 47/225* (2006.01)

(52) U.S. Cl.
CPC .............. *C07C 45/68* (2013.01); *C11B 9/003* (2013.01); *C07C 47/225* (2013.01); *C07C 2601/10* (2017.05); *C07C 2601/16* (2017.05)

(58) Field of Classification Search
CPC ................................ C07C 45/68; C11B 9/003
See application file for complete search history.

(56) References Cited

U.S. PATENT DOCUMENTS

| | | | |
|---|---|---|---|
| 3,963,675 A | 6/1976 | Naegeli | |
| 6,376,458 B1 * | 4/2002 | Winter | C11B 9/0034 512/26 |
| 9,453,182 B1 | 9/2016 | Amorelli et al. | |
| 2018/0282660 A1 * | 10/2018 | Moretti | C11B 9/0034 |

FOREIGN PATENT DOCUMENTS

| | | |
|---|---|---|
| EP | 1054053 A2 | 11/2000 |
| EP | 1529770 A1 | 5/2005 |
| WO | 2018114844 A1 | 6/2018 |

OTHER PUBLICATIONS

International Search Report and Written Opinion for corresponding PCT/EP2019/077791 dated Dec. 19, 2019, 15 Pages.
Andrew G. Capacci et al, "Direct, enantioselective [alpha]-alkylation of aldehydes using simple olefins", Nature Chemistry, Jun. 26, 2017, p. 1073-1077.
Tabbaa I et al, "Addition Radicalaire du Propanal à Divers Alcènes et Cyclènes: Aspects Stériques et Polaires", Bulletin Des Sociétés Chimiques Belges : Vlaamse Chemische Vereniging, Centerick, BE,vol. 92, No. 11-12, Jan. 1, 1983 (Jan. 1, 1983), p. 1011-1018. (Abstract only).
Bône et al., Chimia, (2011), vol. 65, No. 3, p. 177-181.
Lee, H Y Microencapsulation (2002) vol. 19, No. 5, p. 559-556.
Dietrich et al. IV "Amino Resin Microcapsules" Acta Polymerica 41 (1990) No. 2 p. 91-95.
Dietrich et al., "Amino Resin Microcapsules" III Release Properties, Acta Polymerica, vol. 40 (1989), No. 11, pp. 683-690.
Dietrich et al., "Amino Resin Microcapsules" II Preparation and Morphology, Acta Polymerica, 40 (1989), n° 5, 325-331.
Dietrich et al., "Amino Resin Microcapsules" I. Literature and Patent Review, Acta Polymerica, 40 (1989), n° 4, 243-251.

* cited by examiner

*Primary Examiner* — Sikarl A Witherspoon
(74) *Attorney, Agent, or Firm* — Armstrong Teasdale LLP

(57) ABSTRACT

Described herein is a process including alpha alkylation of an aldehyde with a polycyclic olefin followed by a ring opening step in order to provide a compound of formula

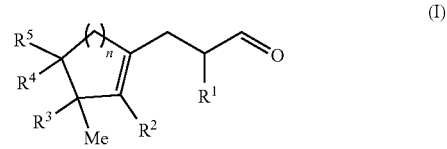

(I)

in a form of any one of its stereoisomers or a mixture thereof and where n represents 1 to 4 and $R^2$ to $R^5$ represent independently of each other, a hydrogen atom or a $C_{1-6}$ linear alkyl group or a $C_{3-6}$ branched alkyl group; and $R^3$ and $R^4$ or $R^5$ or, alternatively, $R^2$ and $R^3$ when taken together form a saturated or unsaturated optionally substituted 5 or 6 membered carbocyclic ring.

17 Claims, No Drawings

CYCLOPROPYL RING OPENING BY ALPHA ALKYLATION OF AN ALDEHYDE WITH A POLYCYCLIC OLEFIN

CROSS-REFERENCE TO RELATED APPLICATIONS

This application is a U.S. National Phase Application of International Patent Application No. PCT/EP2019/077791, filed Oct. 14, 2019, which claims the benefit of priority to European Patent Application No. 18200658.5, filed Oct. 16, 2018, the entire contents of which are hereby incorporated by reference herein.

TECHNICAL FIELD

The present invention relates to the field of organic synthesis and more specifically to the alpha alkylation of an aldehyde with a strained polycyclic olefin comprising a cyclopropyl ring followed by a ring opening of the cyclopropyl ring in order to provide a compound of formula (I). The compound obtainable by such a process, the use of said compound and a perfuming composition or a perfuming consumer product comprising said compound are also part of the present invention.

PRIOR ART

Radical chemistry has been widely reported in the literature, especially the addition of a radical to a polycyclic olefin containing a cyclopropyl as the addition of a radical is followed by a fragmentation; i.e. the opening of the cyclopropyl ring. Said kind of reaction is highly valuable as it allows an access to complicated chemical structures in one step. However, in the majority of reactions, a mixture of regioisomers is obtained especially when the trapping agent is a hydrogen radical making said transformation less interesting as pure chemical compounds are preferable particularly for pharmaceutical industry or flavor and fragrance industry applications wherein regioisomers may have completely different properties.

So, there is a need to develop selective radical reactions leading to one regioisomer, in particular the alpha alkylation of an aldehyde with a strained polycyclic olefin followed by a ring opening step.

The present invention provides a solution to the above problem by performing said alpha alkylation of a linear aldehyde with a polycyclic olefin comprising a cyclopropyl ring in the presence of a photoredox catalyst, a hydrogen atom transfer donor, a secondary amine and light leading to the formation of the less favored kinetic compound of formula (I). The alkylation of an aldehyde in general using a secondary amine and a photoredox catalyst has been reported in Nature Chemistry 2017, 9, 1073-1077. However, no ring opening step is described following the alkylation step of the aldehyde.

To the best of our knowledge, the process according to the present invention has never been reported.

SUMMARY OF THE INVENTION

The invention relates to a novel process providing a compound of formula (I) through the alpha alkylation of an aldehyde with a polycyclic olefin comprising a cyclopropyl ring followed by a ring opening of the cyclopropyl ring which avoids a multistep process while favoring mainly the formation of compound of formula (I) without formation of other possible regioisomers.

A first object of the present invention is a process for the preparation of a compound of formula

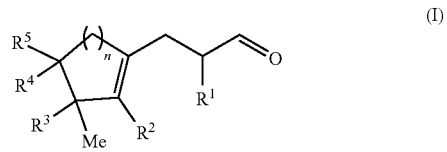

(I)

in the form of any one of its stereoisomers or a mixture thereof and wherein
n represents 1 to 4,
$R^1$ represents a hydrogen or a $C_{1-8}$ linear alkyl group;
$R^2$ to $R^5$ represent independently of each other, a hydrogen atom or a $C_{1-6}$ linear alkyl group or a $C_{3-6}$ branched alkyl group;
$R^3$ and $R^4$ or $R^5$ or, alternatively, $R^2$ and $R^3$ when taken together forms a saturated or unsaturated optionally substituted 5 or 6 membered carbocyclic ring;
comprising the step of an alpha alkylation of an aldehyde of formula $R^1$—$CH_2$—CHO wherein $R^1$ has the same meaning as described above with an olefin compound being a fused or bridged bicyclic or tricyclic compound with a methylene group in alpha position of a cyclopropyl ring junction; i.e attached to one of the carbons alpha to the cyclopropyl ring; said step being performed in the presence of a photoredox catalyst, a hydrogen atom transfer donor, a secondary amine and light.

A second object of the present invention is a compound of formula

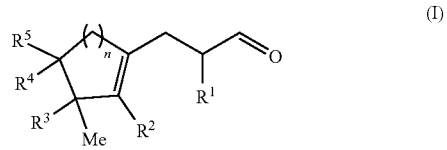

(I)

in the form of any one of its stereoisomers or a mixture thereof and wherein
n represents 1 to 4,
$R^1$ represents a hydrogen or a $C_{1-8}$ linear alkyl group;
$R^2$ to $R^5$ represent independently of each other, a hydrogen atom or a $C_{1-6}$ linear alkyl group or a $C_{3-6}$ branched alkyl group;
$R^3$ and $R^4$ or $R^5$ or, alternatively, $R^2$ and $R^3$ when taken together forms a saturated or unsaturated optionally substituted 5 or 6 membered carbocyclic ring.

A third object of the invention is a method to confer, enhance, improve or modify the odor properties of a perfuming composition or of a perfumed article, which method comprises adding to said composition or article an effective amount of the compound of formula (I) as defined above.

Another object of the invention is the use as a perfuming ingredient of a compound of formula (I) as defined above.

Another object of the invention is a perfuming composition comprising
i) at least a compound of formula (I) as defined above;
ii) at least one ingredient selected from the group consisting of a perfumery carrier and a perfumery base; and
iii) optionally at least one perfumery adjuvant.

A further object of the invention is a perfumed consumer product comprising at least a compound of formula (I) as defined above or a perfuming composition as defined above.

DESCRIPTION OF THE INVENTION

It has now been discovered that the compound of formula (I) can be produced in an advantageous manner by means of the alpha alkylation of an aldehyde with a strained polycyclic olefin comprising a cyclopropyl ring followed by a ring opening of the cyclopropyl ring. Said process gives the kinetically favored compound instead of the Thermodynamically favored one.

A first object of the present invention is a process for the preparation of a compound of formula

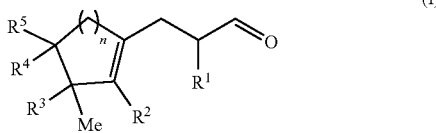

(I)

in the form of any one of its stereoisomers or a mixture thereof and wherein
n represents 1 to 4,
$R^1$ represents a hydrogen or a $C_{1-8}$ linear alkyl group;
$R^2$ to $R^5$ represent independently of each other, a hydrogen atom or a $C_{1-6}$ linear alkyl group or a $C_{3-6}$ branched alkyl group;
$R^3$ and $R^4$ or $R^5$ or, alternatively, $R^2$ and $R^3$ when taken together form a saturated or unsaturated optionally substituted 5 or 6 membered carbocyclic ring;
comprising the step of an alpha alkylation of an aldehyde of formula $R^1$—$CH_2$—CHO wherein $R^1$ has the same meaning as described above with an olefin compound being a fused or bridged bicyclic or tricyclic compound with a methylene group in alpha position of a cyclopropyl ring junction;
said step being performed in the presence of a photoredox catalyst, a hydrogen atom transfer donor, a secondary amine and light.

Said alkylation is followed by a ring opening.

For the sake of clarity, by the expression "any one of its stereoisomers or a mixture thereof", or the similar, it is meant the normal meaning understood by a person skilled in the art, i.e. that the compound of formula (I) can be a pure enantiomer or diastereomer. In other words, the compound of formula (I) may possess several stereocenters and each of said stereocenter can have two different stereochemistries (e.g. R or S). The compound of formula (I) may even be in the form of a pure enantiomer or in the form of a mixture of enantiomers or diastereoisomers. The compound of formula (I) can be in a racemic form or scalemic form. Therefore, the compound of formula (I) can be one stereoisomers or in the form of a composition of matter comprising, or consisting of, various stereoisomers.

By the term "fused or bridged bicyclic or tricylic compound" or similar, it is meant the normal meaning in the art, i.e. for fused bicyclic compound, the compound comprises two ring sharing two adjacent atoms, e.g. decalin, and for bridged bicyclic compound, the compound comprise two ring sharing at least three atoms, e.g. norbornane. According to a particular embodiment, the fused or bridged bicyclic or tricyclic compound does comprise a fused cyclopropyl ring.

By the term "methylene" or similar, it is meant the normal meaning in the art, i.e. a $CH_2$ group linked to one carbon of the cycle by a double bond. In other word, olefin compound has a terminal exo double bond.

By the term "secondary amine", it is meant the normal meaning in the art, i.e. the nitrogen atom is substituted by one hydrogen atom and two groups that are different from hydrogen atoms.

For the sake of clarity, by the term "photoredox catalyst", it is meant the normal meaning in the art, i.e. a catalyst absorbing light to accelerate a chemical reaction by activating organic substrates via a single electron transfer process.

For the sake of clarity, by the expression "hydrogen atom transfer donor", it is meant the normal meaning in the art, i.e. a compound able to provide a hydrogen free radical. Hydrogen atom transfer is also called HAT.

According to any one of the above embodiments, n is 1 to 4. Preferably, n may be 1 to 3, more preferably 1 or 2, typically n is 1.

According to any one of the above embodiments, $R^1$ may be a hydrogen atom or a $C_{1-8}$ linear alkyl group. Preferably, $R^1$ may be a $C_{1-3}$ linear alkyl group; i.e. the aldehyde may be selected from the group consisting of propanal, butanal and pentanal. Preferably, $R^1$ may be a methyl or an ethyl group; i.e. the aldehyde may be selected from the group consisting of propanal and butanal. Even more preferably, $R^1$ may be a methyl group; i.e. the aldehyde may be propanal.

According to any one of the above embodiments, $R^2$ represents a hydrogen atom or a $C_{1-6}$ linear alkyl group or a $C_{3-6}$ branched alkyl group. Preferably, $R^2$ may be a hydrogen atom, a methyl group, an ethyl group or a pentyl group. Even more preferably, $R^2$ may be a hydrogen atom or a methyl group or a pentyl group.

According to any one of the above embodiments, $R^3$ represents a hydrogen atom or a $C_{1-6}$ linear alkyl group or a $C_{3-6}$ branched alkyl group. Preferably, $R^3$ may be a hydrogen atom or a $C_{1-2}$ linear alkyl group or a $C_3$ linear or branched alkyl group. Even more preferably, $R^3$ may be a hydrogen atom or an isopropyl group.

According to any of the above embodiments, $R^4$ represents a hydrogen atom or a $C_{1-6}$ linear alkyl group or a $C_{3-6}$ branched alkyl group. Preferably, $R^4$ may be a hydrogen atom or a $C_{1-2}$ linear alkyl group. Even more preferably, $R^4$ may be a hydrogen or a methyl group.

According to any of the above embodiments, $R^5$ represents a hydrogen atom or a $C_{1-6}$ linear alkyl group or a $C_{3-6}$ branched alkyl group. Preferably, $R^5$ may be a hydrogen atom or a $C_{1-2}$ linear alkyl group. Even more preferably, $R^5$ may be a hydrogen or a methyl group.

According to any of the above embodiments, $R^3$ and $R^4$ or $R^5$ or, alternatively, $R^2$ and $R^3$ when taken together form a saturated or unsaturated optionally substituted 5 or 6 membered carbocyclic ring. Preferably, $R^3$ and $R^4$ or $R^5$ form a saturated or unsaturated optionally substituted 5 or 6 membered carbocyclic ring. By the expression "saturated" and "unsaturated", or the similar, it is meant the normal meaning understood by a person skilled in the art, i.e. that for "saturated" the carbocyclic ring does not comprise a double bond and for "unsaturated" the carbocyclic ring does comprise a double bond but is not an aromatic ring system. By the expression "optionally substituted", or the similar, it is meant that the saturated or unsaturated 5 or 6 membered carbocyclic ring can be substituted with an $C_1$-$C_3$ linear alkyl group or $C_3$ branched alkyl group.

According to any one of the above embodiments, the compound of formula (I) is selected from the group consisting of 2-methyl-3-(2,3,4,4-tetramethylcyclohex-1-en-1-yl)propanal, 2-methyl-3-(3-methyl-2-pentylcyclopent-1-en-1-yl)propanal, 3-(3-isopropyl-3-methylcyclopent-1-en-1-yl)-2-methylpropanal.

According to any one of the above embodiments, the olefin may be a compound of formula

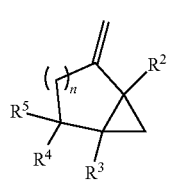

(II)

in the form of any one of its stereoisomers or a mixture thereof; and wherein n represents 1 to 4 and $R^2$ to $R^5$ represent independently of each other, a hydrogen atom or a $C_{1-6}$ linear alkyl group or a $C_{3-6}$ branched alkyl group; $R^3$ and $R^4$ or $R^5$ or, alternatively, $R^2$ and $R^3$ when taken together form a saturated or unsaturated optionally substituted 5 or 6 membered carbocyclic ring.

According to any one of the above embodiments, n is 1 to 4. Preferably, n may be 1 to 3, more preferably 1 or 2, typically n is 1.

According to any embodiments of the invention, and independently of the specific aspects, the compound (I), as well as the compound (II), can be in the form of a racemate or in a form of any one of its stereoisomers or mixture thereof. For the sake of clarity by the term stereoisomer it is intended any diastereomer or enantiomer.

Indeed, the compound (I) or (II) may have several stereogenic centers which can have different stereochemistry (i.e. when two stereogenic centers are present, compound (I) or (II) can have (R,R) or (R,S) configuration. Each of said stereogenic centers can be in a relative or absolute configuration R or S or a mixture thereof or in other words said compound of formula (I) or (II) can be in a form of pure enantiomer or distereoisomer, or in a form of a mixture of stereoisomers.

Non-limiting examples of the olefin may include the compound sabinene, 1,5,5-trimethyl-2-methylenebicyclo[4.1.0]heptane and 2-methylene-1-pentylbicyclo[3.1.0]hexane.

According to any one of the above embodiments, the olefin can be added into the reaction medium of the invention's process in a large range of concentrations. As non-limiting examples, one can cite as olefin concentration values those ranging from about 1 mole equivalent to about 8 mole equivalents, relative to the amount of the aldehyde, preferably from about 1.2 mole equivalents to about 6 mole equivalents, relative to the amount of the aldehyde, 1.8 mole equivalents to about 3.5 mole equivalents, relative to the amount of the aldehyde. The optimum concentration of the olefin will depend, as the person skilled in the art knows, on the nature of the latter, on the nature of the aldehyde, the hydrogen atom transfer donor, the photoredox catalyst and/or the secondary amine, on the reaction temperature as well as on the desired time of reaction.

According to any one of the above embodiments, the photoredox catalyst may be an organic photocatalyst, or an iridium or a ruthenium complex, preferably, an iridium complex.

According to any one of the above embodiments, the photoredox catalyst may have a redox potential of at least 0.8V vs. SCE.

According to a particular embodiment, non-limiting examples of suitable photoredox catalyst may include [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium$^{(III)}$ hexafluorophosphate (corresponding to Ir(dF(CF3)ppy)$_2$(dtbbpy)PF$_6$), [4,4'-Bis(1,1-dimethylethyl)-2,2'-bipyridine-κN1,κN1']bis[3,5-difluoro-2-[5-(methyl)-2-pyridinyl-κN]phenyl-κC]Iridium$^{(III)}$ hexafluorophosphate (corresponding to Ir(dF(Me)ppy)$_2$(dtbbpy)PF$_6$), [4,4'-Bis(1,1-dimethylethyl)-2,2'-bipyridine-κN1,κN1']bis[3,5-difluoro-2-[2-pyridinyl-κN]phenyl-κC]Iridium$^{(III)}$ hexafluorophosphate (corresponding to Ir(dFppy)$_2$(dtbbpy)PF$_6$) or [4,4'-Bis(1,1-dimethylethyl)-2,2'-bipyridine-κN1,κN1']bis[3-fluoro-5-trifluoromethyl-2-[5-(trifluoromethyl)-2-pyridinyl-κN]phenyl-κC]Iridium$^{(III)}$ hexafluorophosphate (corresponding to Ir(FCF$_3$(CF$_3$)ppy)$_2$(dtbbpy)PF$_6$). Preferably, the photoredox catalyst may be [4,4'-Bis(1,1-dimethylethyl)-2,2'-bipyridine-κN1,κN1']bis[3,5-difluoro-2-[5-(trifluoromethyl)-2-pyridinyl-κN]phenyl-κC]Iridium$^{(III)}$ hexafluorophosphate.

According to any one of the above embodiments, the photoredox catalyst can be added into the reaction medium of the invention's process in a large range of concentrations. As non-limiting examples, one can cite as photoredox catalyst concentration values those ranging from about 0.01 mol % to about 10 mol %, relative to the amount of the aldehyde, preferably from about 0.05 mol % to about 5 mol %, relative to the amount of the aldehyde, even more preferably, from about 0.1 mol % to about 1 mol %, relative to the amount of the aldehyde. The optimum concentration of the catalyst will depend, as the person skilled in the art knows, on the nature of the latter, on the nature of the aldehyde, the olefin, the hydrogen atom transfer donor and/or the secondary amine, on the reaction temperature as well as on the desired time of reaction.

According to any one of the above embodiments, the hydrogen atom transfer donor may be any hydrogen atom transfer donor used in radical chemistry such metal hydride compounds such as tin, silicon, sulfur, selenium, boron or phosphorous derivatives or organic compounds such as malonitrile.

According to a particular embodiment, the hydrogen atom transfer donor is a sulfur derivative. Preferably, the hydrogen atom transfer donor is a thiophenol of formula

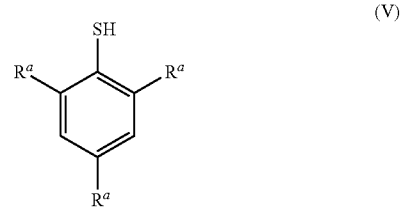

(V)

wherein each $R^a$ represents, independently from each other, a hydrogen atom, a halogen atom, a $C_{1-2}$ linear alkyl group, a $C_{3-4}$ linear or branched alkyl group, a phenyl group optionally substituted by one to five halogen atoms and/or $C_{1-4}$ alkyl or alkoxyl groups or a silyl group trisubstituted with $C_{1-4}$ alkyl groups or an aryl groups; provided that at most two $R^a$ group represent an hydrogen atom. Preferably, the thiophenol may be selected from the group consisting of 2,4,6-trimethylbenzenethiol, 2,4,6-tri-iso-propylbenzenethiol, 2,6-dimethylbenzenethiol, 2,6-di-tert-butyl-4-methylbenzenethiol, 2,6-diisopropylbenzenethiol, 2,4,6-tri-tert-butylbenzenethiol, 4-tert-butylbenzenethiol and 4-fluorobenzenethiol. Preferably, the thiophenol may be selected from the group consisting of 2,4,6-trimethylbenzenethiol, 2,4,6-tri-iso-propylbenzenethiol, 2,6-dimethylbenzenethiol, 2,4,6-tri-tert-butylbenzenethiol, 4-tert-butylbenzenethiol and 4-fluorobenzenethiol. Preferably, the thiophenol may be selected from the group consisting of 2,6-dimethylbenzenethiol, 2,4,6-trimethylbenzenethiol, 2,6-di-tert-butyl-4-methylbenzenethiol, 2,6-diisopropylbenzenethiol, 2,4,6-tri-iso-propylbenzenthiol and 2,4,6-tri-tert-butylbenzenthiol Even more preferably, the thiophenol may be 2,4,6-tri-iso-propylbenzenethiol or 2,4,6-tri-tert-butylbenzenthiol.

According to any one of the above embodiments, the thiophenol can be added into the reaction medium of the invention's process in a large range of concentrations. As non-limiting examples, one can cite as the thiophenol concentration values those ranging from about 0.5 mol % to about 20 mol %, relative to the amount of the aldehyde, preferably from about 1 mol % to about 10 mol %, relative to the amount of the aldehyde. The optimum concentration of the thiophenol will depend, as the person skilled in the art knows, on the nature of the latter, on the nature of the aldehyde, the olefin, the photoredox catalyst and/or the secondary amine, on the reaction temperature as well as on the desired time of reaction.

According to any one of the above embodiments, the secondary amine may be a cyclic or acyclic amine optionally substituted by one to three halogen atoms or an acid or ester group. Preferably the secondary amine may be of formula

(VI)

wherein $R^b$ and $R^c$ represent, when taken separately, independently from each other, a $C_{1-4}$ alkyl group optionally substituted by one to three halogen atoms; or $R^b$ and $R^c$ represent, when taken together, a $C_{2-4}$ linear alkanediyl group optionally substituted by an ester or an acid group. Said secondary amine may be in the form of ammonium salt. Preferably, the secondary amine may be selected from the group consisting of 2-(bis(3,5-bis(trifluoromethyl)phenyl)((trimethylsilyl)oxy)methyl)pyrrolidine, 2,2,2-trifluoro-N-methylethan-1-amine, 2,2,2-trifluoro-N-methylethan-1-aminium chloride, 2,2,2-trifluoro-N-ethylethan-1-amine, 2,2,2-trifluoro-N-ethylethan-1-aminium chloride, bis(2-chloroethyl)amine, bis(2-chloroethyl)aminium chloride, dimethyl amine and dimethylammonium chloride. Preferably, the secondary amine may be selected from the group consisting of 2-(bis(3,5-bis(trifluoromethyl)phenyl)((trimethylsilyl)oxy)methyl)pyrrolidine, 2,2,2-trifluoro-N-methylethan-1-amine, 2,2,2-trifluoro-N-methylethan-1-aminium chloride, bis(2-chloroethyl)amine, bis(2-chloroethyl)aminium chloride, dimethyl amine and dimethylammonium chloride. Even more preferably, the secondary amine may be 2,2,2-trifluoro-N-ethylethan-1-amine or 2,2,2-trifluoro-N-methylethan-1-amine. Even more preferably, the secondary amine may be 2,2,2-trifluoro-N-methylethan-1-amine. The secondary amine may be also in a form of a salt.

According to any one of the above embodiments, the secondary amine can be added into the reaction medium of the invention's process in a large range of concentrations. As non-limiting examples, one can cite as secondary amine concentration values those ranging from about 0.5 mol % to about 20 mol %, relative to the amount of the aldehyde, preferably from about 5 mol % to about 15 mol %, relative to the amount of the aldehyde. The optimum concentration of the secondary amine will depend, as the person skilled in the art knows, on the nature of the latter, on the nature of the aldehyde, the olefin, the photoredox catalyst and/or the hydrogen atom transfer donor, on the reaction temperature as well as on the desired time of reaction.

According to any one of the above embodiments, the light may have a wavelength comprised in the range between 250 nm and 800 nm. Preferably, the light may be UV visible light. Said light may be generated by LED lamp or LED strip.

According to any one of the above embodiments, the invention's process may optionally be carried out in the presence of an inorganic or organic acid such as hydrochloric acid, trifluoroacetic acid or para toluene sulfonic acid.

The reaction can be carried out in the presence or absence of a solvent. When a solvent is required or used for practical reasons, then any solvent current in such reaction type can be used for the purposes of the invention. Solvents with high dielectric constant are preferred. Non-limiting examples of solvents include DMSO, DMPU, DMF, DMA, NMP, acetonitrile, DME, methyl tetrahydrofuran or mixtures thereof. The choice of the solvent is function of the nature of the substrates and/or catalyst and the person skilled in the art is well able to select the solvent most suitable in each case to optimize the reaction.

The invention's process can be carried out at a temperature in the range comprised between 0° C. and 50° C., more. Preferably, the invention's process can be carried out at ambient temperature; i.e. around 25° C. Of course, a person skilled in the art is also able to select the preferred temperature according to the melting and boiling point of the starting and final products as well as the desired time of reaction or conversion.

The invention's process can be carried out under batch or continuous conditions.

Surprisingly, the invention's process avoids the formation of the ketone side product also known as the Kharasch ketone which is formed in the usual radical process. In other words, the invention's process is very selective by providing a compound free of the Kharasch ketone. Without be bound by theory, the invention's process, providing a compound of formula (I), could be divided into several steps; i.e. the reaction of the secondary amine with the aldehyde forming an enamine, then the formation of an enaminyl radical, the addition of said radical to the olefin compound, the opening of the strained cycle and finally the trapping of the radical with the hydrogen atom transfer donor.

Surprisingly, the process according to the present invention provides the kinetically favoured exo ring opening to give selectively, a compound according to formula (I) and avoids the endocyclic ring opening which would give the thermodynamically favoured product being a compound according to formula

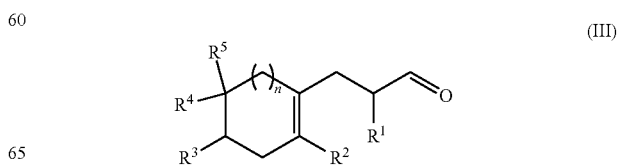

(III)

wherein the meaning of n and $R^1$ to $R^5$ are the same as above.

This means that the process according to the present invention provides selectively a compound according to formula (I) and forms a compound according to formula (III) in not more than 5.0 wt. %, preferably not more than 2.0 wt. %, even more preferably not more than 1.0 wt. %.

By "wt. %" it has to be understood as the weight percent of a compound in a composition. The weight percent compositional aspects of the compositions described herein (e.g., the weight percent of one or more compounds present in a composition) can be determined by gas chromatography (GC), gas chromatography-mass spectroscopy (GC-MS), Raman spectroscopy, nuclear magnetic resonance (NMR) spectroscopy, or any other suitable analytical method known to those of skill in the art.

The compound of formula (I) is novel. So another object of the present invention is compound of formula (I) as defined above. As non-limiting examples of the invention's compound, one can cite 2-methyl-3-(2,3,4,4-tetramethylcyclohex-1-en-1-yl)propanal, 2-methyl-3-(3-methyl-2-pentylcyclopent-1-en-1-yl)propanal, 3-(3-isopropyl-3-methylcyclopent-1-en-1-yl)-2-methylpropanal in a form of any one of its stereoisomers.

Said compound of formula (I) can be used as perfuming ingredient.

So, another object of the present invention is the use of a compound of formula (I) as a perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I) e.g. to impart its typical note.

By "use of a compound" or similar, it has to be understood here also the use of any composition containing a compound (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" it is meant a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic materials, such as porous polymers, cyclodextrines, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As other non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine, such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Other resins are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. in Journal of Microencapsulation, 2002, vol. 19, pages 559-569, international patent publication WO 01/41915 or yet the article of S. Bône et al. in Chimia, 2011, vol. 65, pages 177-181.

By "perfumery base", what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients which are commonly used in perfume formulations, such as:

Aldehydic ingredients: decanal, dodecanal, 2-methyl-undecanal, 10-undecenal, octanal and/or nonenal;

Aromatic-herbal ingredients: eucalyptus oil, camphor, eucalyptol, menthol and/or alpha-pinene;

Balsamic ingredients: coumarine, ethylvanillin and/or vanillin;

Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;

Floral ingredients: Methyl dihydrojasmonate, linalool, Citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-diméthyléthyl)-1-cyclohexyl acetate, verdyl isobutyrate and/or mixture of methyl-ionones isomers;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-Dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, pentadecenolide, 3-Methyl-5-cyclopentadecen-1-one, 1,3,4,6,7,8-hexahydro-4,6,6,7,8,8-hexamethylcyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1, 3-benzodioxol-5-yl)-2-methylpropanal and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" it is meant here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungi or anti irritant agents), abrasives, skin cooling agents, fixatives, insect repellents, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least an invention's compound and at least one perfumery carrier consists of a particular embodiment of the invention as well as a perfuming composition comprising at least one invention's compound; i.e. at least one compound of formula (I), at least one perfumery carrier, at least one perfumery base, and optionally at least one perfumery adjuvant.

According to a particular embodiment, the compositions mentioned above comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the invention's compound would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The invention's compound can also be advantageously used in all the fields of modern perfumery, i.e. fine or functional perfumery, to positively impart or modify the odor of a consumer product into which said compound of formula (I) is added. Consequently, another object of the present invention consists of a perfumed consumer product comprising, as a perfuming ingredient, at least one invention's compound as defined above.

The invention's compound can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care, a wipe, a dish detergent or a hard-surface (e.g. a floor, bath, sanitary or a windows) detergent; a leather care product; a car care product, such as a polish, a wax or a plastic cleaner.

Some of the above-mentioned perfumed consumer products may represent an aggressive medium for the invention's compound, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compound of the invention based on the weight of the composition into which they are incorporated. In the case of perfumed consumer product, typical concentrations are in the order of 0.0001% to 1% by weight, or even more, of the invention's compound based on the weight of the consumer product into which they are incorporated.

EXAMPLES

The invention will now be described in further detail by way of the following examples, wherein the abbreviations have the usual meaning in the art, the temperatures are indicated in degrees centigrade (° C.). NMR spectra were acquired using either a Bruker Avance II Ultrashield 400 plus operating at 400 MHz, ($^1$H) and 100 MHz ($^{13}$C) or a Bruker Avance III 500 operating at 500 MHz ($^1$H) and 125 MHz ($^{13}$C) or a Bruker Avance III 600 cryoprobe operating at 600 MHz ($^1$H) and 150 MHz ($^{13}$C). Spectra were internally referenced relative to tetramethyl silane 0.0 ppm. $^1$H NMR signal shifts are expressed in δ ppm, coupling constants (J) are expressed in Hz with the following multiplicities: s, singlet; d, doublet; t, triplet; q, quartet; m, multiplet; b, broad (indicating unresolved couplings) and were interpreted using Bruker Topspin software. $^{13}$C NMR data are expressed in chemical shift δ ppm and hybridization from DEPT 90 and DEPT 135 experiments, C, quaternary; CH, methine; CH$_2$, methylene; CH$_3$, methyl.

Preparation of Compounds Using the Invention's Process

Example 1

A glass tube with water jacket was charged with 2-methylene-1-pentylbicyclo[3.1.0]hexane (3.28 g, 20 mmol), [4,4'-Bis(1,1-dimethylethyl)-2,2'-bipyridine-N1,N1']bis[3,5-difluoro-2-[5-(trifluoromethyl)-2-pyridinyl-N]phenyl-C]

Iridium$^{(III)}$ hexafluorophosphate (0.011 g, 0.01 mmol), 2,4,6-tri-tert-butylbenzenethiol (0.070 g, 0.25 mmol), HCl (0.08 ml, 0.5 mmol), H$_2$O (0.54 ml, 30 mmol), DME (5 mL). Finally, propionaldehyde (0.58 g, 10 mmol) and 2,2,2-trifluoro-N-methylethanamine (0.11 g, 1.0 mmol) were added.

The mixture was irradiated with a blue LED lamp and stirred at RT for 24 h. The aqueous layer was decanted, then extracted with diethyl ether then the organic phase was washed twice with water, dried over magnesium sulfate, and the solvents were evaporated under vacuum. The crude product was purified by Kügelrohr bulb to bulb distillation (0.1 mbar, 120° C.) to afford 2-methyl-3-(3-methyl-2-pentylcyclopent-1-en-1-yl)propanal as a colorless oil (1.51 g, 6.1 mmol, 58% yield). Compared to all the similar processes describe in the literature, this aldehyde was obtained in a surprisingly, selectivity manner (selectivity higher than 95%) as a result of the kinetically favored exo ring cyclopropyl opening of the 2-methylene-1-pentylbicyclo[3.1.0]hexane.

An olfative evaluation of the compound has shown an interesting watery olfactive note.

$^1$H NMR (CDCl$_3$, 500 MHz), mixture diastereoisomers: 0.88 (t, J=7.2 Hz, 6H), 0.97 (d, J=6.7 Hz, 3H), 0.98 (d, J=7.0 Hz, 3H), 1.02 (d, J=7.0 Hz, 3H), 1.03 (d, J=6.7 Hz, 3H), 1.18-1.35 (m, 12H), 1.36-1.44 (m, 2H), 1.88-1.95 (m, 2H), 1.97-2.18 (m, 8H), 2.19-2.29 (m, 2H), 2.37-2.52 (m, 4H), 2.63-2.71 (m, 2H), 9.63 (d, J=1.9 Hz, 1H), 9.64 (d, J=1.9 Hz, 1H) ppm.

$^{13}$C NMR (CDCl$_3$, 125 MHz), mixture of diastereoisomers: 205.35 (CH), 205.31 (CH), 143.33 (C), 143.23 (C), 130.98 (C), 130.95 (C), 45.06 (CH), 45.00 (CH), 41.40 (CH), 41.38 (CH), 33.98 (CH$_2$), 33.94 (CH$_2$), 32.07 (CH$_2$), 32.02 (CH$_2$), 31.25 (2CH$_2$), 29.87 (CH$_2$), 29.64 (CH$_2$), 27.79 (CH$_2$), 27.74 (CH$_2$), 26.21 (CH$_2$), 26.20 (CH$_2$), 22.59 (2CH$_2$), 19.47 (CH$_3$), 19.39 (CH$_3$), 14.06 (2CH$_3$), 13.33 (CH$_3$), 13.09 (CH$_3$) ppm.

Example 2

A glass tube equipped with a water jacket was charged with (1S,5S)-1-isopropyl-4-methylenebicyclo[3.1.0]hexane (20.44 g, 150 mmol), [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium$^{(III)}$ hexafluorophosphate (0.056 g, 0.05 mmol), 2,4,6-tri-tert-butylbenzenethiol (0.35 g, 1.25 mmol), HCl (0.42 ml, 2.5 mmol), H$_2$O (2.7 ml, 150 mmol), DME (25 mL). Finally propionaldehyde (2.90 g, 50 mmol) and 2,2,2-trifluoro-N-methylethanamine (0.56 g, 5 mmol) were added.

The mixture was stirred at RT and placed under Blue LED lamp irradiation for 24 h. The aqueous layer was decanted, diethyl ether was added and the organic phase was washed twice with water, dried over magnesium sulfate, and the solvents evaporated in vacuo. The crude product was purified by Fisher distillation (0.5 mbar, 120° C.) to afford 3-[(3S)-3-isopropyl-3-methyl-1-cyclopenten-1-yl]-2-methylpropanal as a colorless oil (2.90 g, 14.6 mmol, 29% yield). The compound resulting from the endo ring cyclopropyl opening (i.e. thermodynamically favored compound) was not observed.

The compound obtained was olfactively evaluated and described as having an aldehydic and watery note.

$^1$H NMR (CDCl$_3$, 500 MHz), mixture diastereoisomers: 0.81 (d, J=7.0 Hz, 6H), 0.83 (d, J=6.9 Hz, 6H), 0.93 (s, 3H), 0.94 (s, 3H), 1.07 (d, J=6.9 Hz, 6H), 1.46-1.51 (m, 2H), 1.52-1.57 (m, 2H), 1.76-1.82 (m, 2H), 2.08-2.30 (m, 6H), 2.41-2.48 (m, 2H), 2.48-2.55 (m, 2H), 5.22-5.24 (m, 2H), 9.63 (d, J=1.6 Hz, 1H), 9.64 (d, J=1.6 Hz, 1H) ppm.

$^{13}$C NMR (CDCl$_3$, 125 MHz), mixture of diastereoisomers: 205.12 (CH), 205.11 (CH), 138.42 (C), 138.39 (C), 135.48 (CH), 135.45 (CH), 51.95 (C), 51.93 (C), 44.68 (CH), 36.41 (CH), 34.63 (CH$_2$), 34.57 (CH$_2$), 34.28 (CH$_2$), 32.43 (CH$_2$), 32.40 (CH$_2$), 23.55 (CH$_3$), 23.47 (CH$_3$), 18.42 (CH$_3$), 18.39 (CH$_3$), 18.15 (CH$_3$), 13.50 (CH$_3$), 13.45 (CH$_3$) ppm.

Example 3

A glass tube equipped with a water jacket was charged with 1,5,5-trimethyl-2-methylenebicyclo[4.1.0]heptane (0.9 g, 6 mmol), [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium$^{(III)}$ hexafluorophosphate (0.011 g, 0.01 mmol), 2,4,6-tri-tert-butylbenzenethiol (0.070 g, 0.25 mmol), HCl (0.08 ml, 0.5 mmol), H$_2$O (0.54 ml, 30 mmol), DME (25 mL). Finally propionaldehyde (0.58 g, 10 mmol) and 2,2,2-trifluoro-N-methylethanamine (0.11 g, 1.0 mmol) were added.

The mixture was irradiated with blue LED light and stirred at RT for 24 h. The aqueous layer was decanted, diethylether was added and the organic phase was washed twice with water, dried over magnesium sulfate, and the solvents were evaporated under vacuum. The crude product was purified by column chromatography (heptane/EtOAc 9/1) and then by Kügelrohr bulb to bulb distillation (0.1 mbar, 120° C.) to afford 2-methyl-3-(2,3,4,4-tetramethylcyclohex-1-en-1-yl)propanal as a colorless oil (0.25 g, 1.2 mmol, 40% yield). The compound resulting from the endo ring cyclopropyl opening (i.e. thermodynamically favored compound) was not observed.

The olfactive profile of the compound was evaluated as showing an interesting watery olfactive note.

$^1$H NMR (CDCl$_3$, 500 MHz), mixture of diastereoisomers: 0.84 (s, 3H), 0.84 (s, 3H), 0.86 (s, 3H), 0.86 (s, 3H), 0.90 (d, J=7.0 Hz, 3H), 0.91 (d, J=6.9 Hz, 3H), 1.05 (d, J=6.8 Hz, 6H), 1.14-1.18 (m, 2H), 1.24-1.31 (m, 4H), 1.46-1.53 (m, 2H), 1.64 (m, 6H), 1.83-1.99 (m, 2H), 2.09-2.14 (m, 2H), 2.30-2.36 (m, 2H), 2.49-2.57 (m, 2H), 9.6 (d, J=2.3 Hz, 2H) ppm.

$^{13}$C NMR (CDCl$_3$, 125 MHz), mixture of diastereoisomers: 205.43 (2×CH), 133.11 (C), 133.08 (C), 124.54 (C), 124.47 (C), 45.96 (CH), 45.91 (CH), 45.52 (CH), 45.41 (CH), 34.32 (CH$_2$), 34.26 (CH$_2$), 31.65 (C), 31.63 (C), 31.34 (CH2), 31.18 (CH$_2$), 27.46 (CH$_2$), 27.40 (CH$_2$), 27.14 (2×CH$_3$), 27.03 (2×CH$_3$), 18.88 (CH$_3$), 18.85 (CH$_3$), 15.36 (CH$_3$), 15.31 (CH$_3$), 13.25 (CH$_3$), 13.12 (CH$_3$) ppm.

The invention claimed is:
1. A process for the preparation of a compound of formula

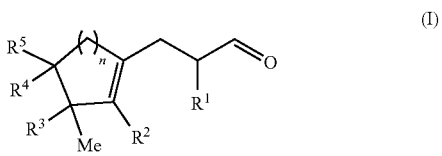

(I)

in a form of any one of its stereoisomers or a mixture thereof and wherein n represents 1 to 4, R$^1$ represents a hydrogen or a C$_{1-8}$ linear alkyl group;

$R^2$ to $R^5$ represent independently of each other, a hydrogen atom or a $C_{1-6}$ linear alkyl group or a $C_{3-6}$ branched alkyl group; and $R^3$ and $R^4$ or $R^5$ or, alternatively, $R^2$ and $R^3$ when taken together form a saturated or unsaturated optionally substituted 5 or 6 membered carbocyclic ring;

comprising the step of an alpha alkylation of an aldehyde of formula $R^1$—$CH_2$—CHO wherein $R^1$ has the same meaning as described above with an olefin compound being a fused or bridged bicyclic or tricyclic compound with a methylene group in alpha position of a cyclopropyl ring junction;

said step being performed in the presence of a photoredox catalyst, a hydrogen atom transfer donor, a secondary amine and light.

2. The process according to claim 1, wherein the aldehyde is propanal.

3. The process according to claim 1, wherein the olefin is a compound of formula

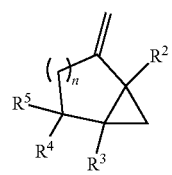

(II)

in a form of any one of its stereoisomers or a mixture thereof; and wherein n represents 1 to 4 and $R^2$ to $R^5$ represent independently of each other, a hydrogen atom or a $C_{1-6}$ linear alkyl group or a $C_{3-6}$ branched alkyl group; and $R^3$ and $R^4$ or $R^5$ or, alternatively, $R^2$ and $R^3$ when taken together form a saturated or unsaturated optionally substituted 5 or 6 membered carbocyclic ring.

4. The process according to claim 1, wherein the photoredox catalyst is an organic photocatalyst, an iridium complex, or a ruthenium complex.

5. The process according to claim 1, wherein the hydrogen atom transfer donor is a thiophenol of formula

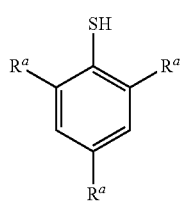

(V)

wherein each $R^a$ represents, independently from each other, a hydrogen atom, a halogen atom, a $C_{1-2}$ linear alkyl group, a $C_{3-4}$ linear or branched alkyl group, a phenyl group optionally substituted by one to five halogen atoms and/or $C_{1-4}$ alkyl or alkoxyl groups or a silyl group trisubstituted with $C_{1-4}$ alkyl groups or an aryl group; provided that at most two $R^a$ group represent a hydrogen atom.

6. The process according to claim 1, wherein the compound of formula (I) is selected from the group consisting of 2-methyl-3-(2,3,4,4-tetramethylcyclohex-1-en-1-yl)propanal, 2-methyl-3-(3-methyl-2-pentylcyclopent-1-en-1-yl)propanal, 3-(3-isopropyl-3-methylcyclopent-1-en-1-yl)-2-methylpropanal, and 3-((R)-3-isopropyl-3-methylcyclopent-1-en-1-yl)-2-methylpropanal.

7. A compound of formula

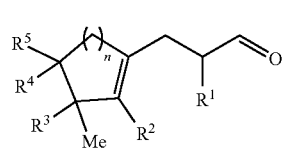

(I)

in a form of any one of its stereoisomers or a mixture thereof and wherein n represents 1 to 4; $R^1$ represents a hydrogen or a $C_{1-8}$ linear alkyl group and $R^2$ to $R^5$ represent independently of each other, a hydrogen atom or a $C_{1-6}$ linear alkyl group or a $C_{3-6}$ branched alkyl group; and $R^3$ and $R^4$ or $R^5$ or, alternatively, $R^2$ and $R^3$ when taken together form a saturated or unsaturated optionally substituted 5 or 6 membered carbocyclic ring.

8. A method to confer, enhance, improve or modify the odor properties of a perfuming composition or of a perfumed article, which method comprises adding to said composition or article an effective amount of the compound of formula (I) as defined in claim 7.

9. A perfuming composition comprising
i) at least one compound of formula (I) as defined in claim 7;
ii) at least one ingredient selected from the group consisting of a perfumery carrier and a perfumery base; and
iii) optionally at least one perfumery adjuvant.

10. A perfumed consumer product comprising at least one compound of formula (I) as defined in claim 7.

11. The perfumed consumer product according to claim 10, wherein the product is a perfume, a fabric care product, a body-care product, a cosmetic preparation, a skin-care product, an air care product or a home care product.

12. The perfumed consumer product according to claim 11, wherein the perfumed consumer product is a fine perfume, a splash or eau de perfume, a cologne, an shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, shower or bath mousse, oil or gel, or a foot/hand care products, a hygiene product, an air freshener, a "ready to use" powdered air freshener, a mold remover, a furnisher care, a wipe, a dish detergent or hard-surface detergent, a leather care product, or a car care product.

13. The process according to claim 1, wherein the photoredox catalyst is an iridium complex.

14. The process according to claim 1, wherein the compound of formula (I) is 3-((R)-3-isopropyl-3-methylcyclopent-1-en-1-yl)-2-methylpropanal.

15. A perfumed consumer product comprising a perfuming composition as defined in claim 9.

16. The perfumed consumer product according to claim 15, wherein the product is a perfume, a fabric care product, a body-care product, a cosmetic preparation, a skin-care product, an air care product, or a home care product.

17. The perfumed consumer product according to claim 16, wherein the perfumed consumer product is a fine perfume, a splash or eau de perfume, a cologne, an shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, shower or bath mousse, oil or gel, or a foot/hand care products, a hygiene product, an air freshener, a "ready to use" powdered air freshener, a mold remover, a furnisher care, a wipe, a dish detergent or hard-surface detergent, a leather care product, or a car care product.

* * * * *